United States Patent
Yi

(10) Patent No.: US 11,246,900 B2
(45) Date of Patent: Feb. 15, 2022

(54) ANTI-INFLAMMATORY, ANALGESIC AND FAST-HEALING EXTERNAL TRADITIONAL CHINESE MEDICINE PREPARATION AND ITS PREPARATION METHOD

(71) Applicant: SHANGHAI HOEHER CO., LTD., Shanghai (CN)

(72) Inventor: Cuilin Yi, Shanghai (CN)

( * ) Notice: Subject to any disclaimer, the term of this patent is extended or adjusted under 35 U.S.C. 154(b) by 710 days.

(21) Appl. No.: 15/740,808

(22) PCT Filed: Jun. 6, 2017

(86) PCT No.: PCT/CN2017/087249
§ 371 (c)(1),
(2) Date: Dec. 29, 2017

(87) PCT Pub. No.: WO2018/113200
PCT Pub. Date: Jun. 28, 2018

(65) Prior Publication Data
US 2019/0328814 A1    Oct. 31, 2019

(30) Foreign Application Priority Data

Dec. 21, 2016  (CN) .......................... 201611194018.5
Apr. 24, 2017  (CN) .......................... 201710272867.6

(51) Int. Cl.
| | | |
|---|---|---|
| *A61K 36/66* | (2006.01) | |
| *A61K 9/00* | (2006.01) | |
| *A61K 35/02* | (2015.01) | |
| *A61K 35/618* | (2015.01) | |
| *A61K 36/10* | (2006.01) | |
| *A61K 36/28* | (2006.01) | |
| *A61K 36/714* | (2006.01) | |
| *A61K 36/716* | (2006.01) | |

(52) U.S. Cl.
CPC ............ *A61K 36/66* (2013.01); *A61K 9/0014* (2013.01); *A61K 35/02* (2013.01); *A61K 35/618* (2013.01); *A61K 36/10* (2013.01); *A61K 36/28* (2013.01); *A61K 36/714* (2013.01); *A61K 36/716* (2013.01); *A61K 2236/333* (2013.01)

(58) Field of Classification Search
None
See application file for complete search history.

(56) References Cited

PUBLICATIONS

CN101361819A (English translation retrieved from Google Patents). (Year: 2009).*
CN103720623A (English translation retrieved from Google Patents) (Year: 2015).*
Borten, P., Fu Hai Shi, Chinese Herbal Medicine; http://chineseherbinfo.com/fu-hai-shi-fu-shi-hai-fu-shi-pumice-or-occasionally-costazia-skeleton-an-aquatic-invertebrate-similar-to-coral-float. (Year: 2013).*
Wang, et al., Chinese Medicine Modern Practice Annals of Traditional Chinese Medicine, vol. 1, Chapter 4, "The Rationale of Combination Drug Formulas in Traditional Chinese Medicine," pp. 43-51. (Year: 2005).*
Farquhar, J., Knowing Practice, Chapter 3, "The Clinical Encounter Observed," pp. 41-59. (Year: 1994).*

* cited by examiner

*Primary Examiner* — Michael Barker
(74) *Attorney, Agent, or Firm* — Bayramoglu Law Offices LLC

(57) ABSTRACT

The present invention provides an anti-inflammatory, analgesic and fast-healing external traditional Chinese medicine preparation and its preparation method. The traditional Chinese medicine preparation includes following components in parts by weight: 30-80 parts of corydalis tuber, 20-90 parts of maifanitum, 20-50 parts of radix aconiti kusnezoffii praeparata, 10-45 parts of common clubmoss herb, 10-40 parts of *clematis* root, 10-40 parts of safflower, 5-40 parts of bryozoatum and 5-35 parts of oyster shell. The traditional Chinese medicine preparation has advantages of unique prescription, reasonable ratio, advanced preparation process, high active ingredient content, fast absorption, no irritation of ethanol preparation to the skin, convenient use, direct effect on the lesion location, fast and significant curative effect and no adverse effect on organs of the human body.

4 Claims, No Drawings

ANTI-INFLAMMATORY, ANALGESIC AND FAST-HEALING EXTERNAL TRADITIONAL CHINESE MEDICINE PREPARATION AND ITS PREPARATION METHOD

CROSS REFERENCE OF RELATED APPLICATION

This is a U.S. National Stage under 35 U.S.C. 371 of the International Application PCT/CN2017/087249, filed Jun. 6, 2017, which claims priority under 35 U.S.C. 119(a-d) to CN 201611194018.5, filed Dec. 21, 2016; and CN 201710272867.6, filed Apr. 24, 2017.

BACKGROUND OF THE PRESENT INVENTION

Field of Invention

The present invention relates to the technical field of external traditional Chinese medicine preparation, and more particularly to an anti-inflammatory, analgesic and fast-healing external traditional Chinese medicine preparation and its preparation method. The traditional Chinese medicine preparation is used to treat the pain of bone and joint, muscle and soft tissue and rapidly heal superficial wounds.

Description of Related Arts

The pain of bone and joint, muscle is a large type of disease. According to a survey conducted by the World Health Organization, there are about 350 million people in the world currently suffering from various types of rheumatoid bone diseases which are the largest type of diseases in the medical field. However, there are about 130 million people in China suffering from these diseases. According to statistics, 65% of the patients are not effectively treated. At present, there are many ways to treat such diseases, mainly including physical therapy, drug therapy and surgical treatment for severe diseases. Due to the long time in the physical therapy, large trauma and high cost in the surgical treatment, and absorption through the gastrointestinal tract, great side effect and slow effect in the oral medication, patients mostly select external traditional Chinese medicine for treatment. At present, the external traditional Chinese medicine preparation for treating such diseases mainly includes the tincture, ointment and spray. Due to the different prescriptions, dosage forms and preparation processes of each traditional Chinese medicine preparation, the therapeutic effect varies greatly. Currently, there are few external therapeutic drugs commonly used for anti-inflammation and relieving pain of bone and joint, muscle and soft tissue. In addition, the external medication effect is generally limited, and there is basically no the situation that the lesion can be completely cured and the coordination of oral medication and external medication is mostly required; while the side effect of oral medication on the human body is significantly greater than that of external medication and it will take a long time to cure the lesion with slow effect.

Moreover, for superficial wounds that are neat and clean and the bleeding is not serious without being sutured, the adhesive bandage has the function of temporary hemostasis and wound protection and is the most commonly used surgery drug in people's lives. At present, the annual production of band-aid in the world has exceeded 100 billion and reached about 7 billion in China. However, the band-aid should not be used for a long period of time as it will whiten and soften the wounds and the skin around the wounds, resulting in secondary bacterial infection and worsening of the wounds.

Furthermore, all the anti-inflammatory and analgesic external traditional Chinese medicine preparations currently on the market contain only anti-inflammatory ingredients, analgesic ingredients and ingredients for relaxing tendons and activating collaterals, and lack the nutrients that can nourish the injured cells and tissues and promote cell regeneration and repair.

SUMMARY OF THE PRESENT INVENTION

In view of the defects in the prior art, the present invention provides an anti-inflammatory, analgesic and fast-healing external traditional Chinese medicine preparation and its preparation method. It has characteristics of novel prescription, unique preparation process, fast transdermal absorption, obvious anti-inflammatory and analgesic effect and wound healing effect, no side effect as well as simple and convenient use. Meanwhile, a variety of nutrients contained in the product can also nourish the injured cells and tissues and rapidly promote cell regeneration and repair. The product is significantly better than the similar products currently on the market in the treatment of bone and joint, muscle and soft tissue pain and fast healing of superficial wounds. It is worth mentioning that the product can not only have the anti-inflammatory and analgesic effect through the fast transdermal absorption to the affected part, but also have the effect of rapid hemostasis and healing for superficial wounds. It is more safe, convenient and effective than the band-aid, and the liquid is colorless and odorless and can be used for any allergic constitution.

The object of the present invention is realized by means of the following technical solution:

The present invention provides an anti-inflammatory, analgesic and fast-healing external traditional Chinese medicine preparation, which comprises following components in parts by weight:

| | |
|---|---|
| corydalis tuber | 30-80; |
| maifanitum | 20-90; |
| radix aconiti kusnezoffii praeparata | 20-50; |
| common clubmoss herb | 10-45; |
| clematis root | 10-40; |
| safflower | 10-40; |
| bryozoatum | 5-40; and |
| oyster shell | 5-35. |

If the content of each of the above components is out of the range, the effect of the present invention cannot be obtained.

Preferably, the anti-inflammatory, analgesic and fast-healing external traditional Chinese medicine preparation comprises the following components in parts by weight:

| | |
|---|---|
| corydalis tuber | 30-50; |
| maifanitum | 65-90; |
| radix aconiti kusnezoffii praeparata | 25-45; |
| common clubmoss herb | 15-30; |
| clematis root | 15-30; |
| safflower | 10-25; |
| bryozoatum | 5-30; and |
| oyster shell | 5-20. |

The present invention also provides a method for preparing an anti-inflammatory, analgesic and fast-healing external traditional Chinese medicine preparation which comprises steps of:

(A1) weighing corydalis tuber, radix aconiti kusnezoffii praeparata, common clubmoss herb, *clematis* root and safflower based on a raw material ratio, breaking cell wall and smashing the corydalis tuber, radix aconiti kusnezoffii praeparata, common clubmoss herb, *clematis* root and safflower, mixing the smashed raw materials, extracting active ingredients thereof in a closed temperature controlled extraction tank, obtaining an extracting solution, distilling the extracting solution under reduced pressure, and obtaining an alcohol-free concentrate;

(A2) mixing after smashing maifanitum, bryozoatum and oyster shell, extracting active ingredients thereof in the closed temperature controlled extraction tank, and obtaining an extracting solution; and (A3) mixing the alcohol-free concentrate obtained in the step (A1) with the extracting solution obtained in the step (A2), obtaining a mixed solution, shearing the mixed solution with an ultra-high shear homogenizer at a high speed for 20 minutes, and obtaining the anti-inflammatory, analgesic and fast-healing external traditional Chinese medicine liniment.

Preferably, in the step (A1), an extraction temperature is in a range of 40-60° C. and an extraction solvent is ethanol with a mass fraction in a range of 50-70% or water.

More preferably, in the step (A1), the extraction temperature is in the range of 40-60° C. and the extraction solvent is the ethanol with the mass fraction of 60%.

Preferably, in the step (A2), an extraction temperature is in a range of 40-60° C. and an extraction solvent is sulfuric acid with a mass fraction in a range of 2-10%, acetic acid with a mass fraction in a range of 2-20% or water.

More preferably, in the step (A2), the extraction temperature is in the range of 40-60° C. and the extraction solvent is the sulfuric acid with the mass fraction of 10%.

Preferably, a dosage form of the preparation comprises liniment, spray and ointment.

The use method of the anti-inflammatory, analgesic and fast-healing external traditional Chinese medicine preparation according to the present invention includes external proper injunction, spraying, smearing and applying. When the anti-inflammatory, analgesic and fast-healing external traditional Chinese medicine preparation is the liniment, a few drops of the liquid medicine are directly dropped on the affected part and rubbed repeatedly with fingers until completely absorbed; the steps are repeated for 3-4 times and 2-3 times a day will be required.

Compared with the prior art, the present invention has the following beneficial effects:

The anti-inflammatory, analgesic and fast-healing external traditional Chinese medicine preparation according to the present invention takes the anti-inflammation, relieving pain and nourishing and repair of the injured cells and tissues as a basis for the prescription, and has the advantages of unique prescription, reasonable ratio, advanced preparation process, high active ingredient content, fast absorption, no irritation of ethanol preparation to the skin, convenient use, direct effect on the lesion location, fast and significant curative effect and no adverse effect on organs of the human body. The traditional Chinese medicine preparation is very effective in treating the pain of bone and joint, muscle and soft tissue, and the affected part can basically achieve a satisfactory degree of recovery after continuous use for a period of time. For the crowd of small superficial wounds, the traditional Chinese medicine preparation according to the present invention has a prominent effect in anti-inflammation, relieving pain and healing wounds.

The traditional Chinese medicine preparation according to the present invention is negative after repeated skin irritation test and skin allergy test, so patients do not need to worry about allergies. Therefore, the traditional Chinese medicine preparation according to the present invention has fast and significant curative effect and no allergic reactions, is safe and nontoxic, and has broad development prospects and good social benefits.

DETAILED DESCRIPTION OF THE PREFERRED EMBODIMENT

The present invention is described in detail as follows with reference to specific embodiments. The following embodiments will help further understanding of the present invention for those skilled in the art, and not in any way limit the present invention. It shall be noted that several variants and improvements can be made without departing from concept of the present invention for ordinary persons skilled in the art. All these fall within the protection scope of the present invention.

The following embodiments provide an anti-inflammatory, analgesic and fast-healing external traditional Chinese medicine preparation, which comprises following components in parts by weight:

| | |
|---|---|
| corydalis tuber | 30-80; |
| maifanitum | 20-90; |
| radix aconiti kusnezoffii praeparata | 20-50; |
| common clubmoss herb | 10-45; |
| clematis root | 10-40; |
| safflower | 10-40; |
| bryozoatum | 5-40; and |
| oyster shell | 5-35. |

The following embodiments also provide a method for preparing an anti-inflammatory, analgesic and fast-healing external traditional Chinese medicine preparation, which comprises steps of:

(A1) weighing corydalis tuber, radix aconiti kusnezoffii praeparata, common clubmoss herb, *clematis* root and safflower based on a raw material ratio, breaking cell wall and smashing the corydalis tuber, radix aconiti kusnezoffii praeparata, common clubmoss herb, *clematis* root and safflower, mixing the smashed raw materials, extracting active ingredients thereof in a closed temperature controlled extraction tank by taking ethanol with a mass fraction in a range of 50-70% or water as a solvent, obtaining an extracting solution, distilling the extracting solution under reduced pressure, and obtaining an alcohol-free concentrate;

(A2) mixing after smashing maifanitum, bryozoatum and oyster shell, extracting active ingredients thereof in the closed temperature controlled extraction tank by taking sulfuric acid with a mass fraction in a range of 2-10% or acetic acid with a mass fraction in a range of 2-20% or water as the solvent, and obtaining an extracting solution; and (A3) mixing the alcohol-free concentrate obtained in the step (A1) with the extracting solution obtained in the step (A2), obtaining a mixed solution, shearing the mixed solution with an ultra-high shear homogenizer at a high speed for 20 minutes, and obtaining the anti-inflammatory, analgesic and fast-healing external traditional Chinese medicine preparation.

In the step (A1), an extraction temperature is in a range of 40-60° C. and an extraction solvent is the ethanol with the mass fraction in the range of 50-70% or water.

In the step (A2), an extraction temperature is in a range of 40-60° C. and an extraction solvent is the sulfuric acid with the mass fraction in the range of 2-10% or acetic acid with the mass fraction in the range of 2-20% or water.

A dosage form of the preparation comprises liniment, spray and ointment.

Embodiment 1

The embodiment provides an anti-inflammatory, analgesic and fast-healing external traditional Chinese medicine liniment, wherein the traditional Chinese medicine liniment is prepared from the following raw materials in parts by weight:

| | |
|---|---|
| corydalis tuber | 40; |
| maifanitum | 90; |
| radix aconiti kusnezoffii praeparata | 35; |
| common clubmoss herb | 30; |
| clematis root | 28; |
| safflower | 25; |
| bryozoatum | 20; and |
| oyster shell | 10. |

A method for preparing the above anti-inflammatory, analgesic and fast-healing external traditional Chinese medicine liniment comprises steps of: (step 1) weighing the corydalis tuber, radix aconiti kusnezoffii praeparata, common clubmoss herb, *clematis* root and safflower based on a raw material ratio, breaking cell wall and smashing the corydalis tuber, radix aconiti kusnezoffii praeparata, common clubmoss herb, mixing the smashed raw materials, extracting active ingredients thereof in a closed temperature controlled extraction tank at 40° C. by taking ethanol with a mass fraction of 60% as a solvent, obtaining an extracting solution, concentrating the extracting solution under reduced pressure, and obtaining an alcohol-free concentrate; (step 2) mixing after smashing the maifanitum, bryozoatum and oyster shell, extracting active ingredients thereof in the closed temperature controlled extraction tank at 40° C. by taking sulfuric acid with a mass fraction of 10% as the solvent, and obtaining an extracting solution; and (step 3) mixing the alcohol-free concentrate obtained in the (step 1) with the extracting solution obtained in the (step 2), obtaining a mixed solution, shearing the mixed solution with an ultra-high shear homogenizer at a high speed for 20 minutes, and obtaining the anti-inflammatory, analgesic and fast-healing external traditional Chinese medicine liniment.

The use method of the above anti-inflammatory, analgesic and fast-healing external traditional Chinese medicine liniment according to the present invention is the external proper injunction. A few drops of the liquid medicine are directly dropped on the affected part and rubbed repeatedly with fingers until completely absorbed. The steps are repeated for 3-4 times and 2-3 times a day will be required.

Embodiment 2

The embodiment provides an anti-inflammatory, analgesic and fast-healing external traditional Chinese medicine liniment, wherein the traditional Chinese medicine liniment is prepared from the following raw materials in parts by weight:

| | |
|---|---|
| corydalis tuber | 30; |
| maifanitum | 80; |
| radix aconiti kusnezoffii praeparata | 25; |
| common clubmoss herb | 20; |
| clematis root | 15; |
| safflower | 15; |
| bryozoatum | 30; and |
| oyster shell | 5. |

A method for preparing the above anti-inflammatory, analgesic and fast-healing external traditional Chinese medicine liniment is the same as that of embodiment 1.

Embodiment 3

The embodiment provides an anti-inflammatory, analgesic and fast-healing external traditional Chinese medicine liniment, wherein the traditional Chinese medicine liniment is prepared from the following raw materials in parts by weight:

| | |
|---|---|
| corydalis tuber | 50; |
| maifanitum | 65; |
| radix aconiti kusnezoffii praeparata | 45; |
| common clubmoss herb | 15; |
| clematis root | 30; |
| safflower | 10; |
| bryozoatum | 5; and |
| oyster shell | 20. |

A method for preparing the above anti-inflammatory, analgesic and fast-healing external traditional Chinese medicine liniment is the same as that of embodiment 1.

For the anti-inflammatory, analgesic and fast-healing external traditional Chinese medicine liniment prepared in the above embodiments 1-3, the treatment effective rate reaches about 98% through the observation and analysis of trial of 46 cases, including 7 cases of cervical bone hyperplasia, 9 cases of lumbar disc herniation, 6 cases of scapulohumeral periarthritis, 10 cases of senile knee joint pain, 3 cases of gout, 5 cases of soft tissue and tendon injury and 6 cases of finger and leg superficial trauma. The treatment effective rate is judged based on the following conditions: the pain and numbness of waist and legs and bone and joint relieve or disappear; the stiffness or activity limitation of bone and joint significantly relieves or completely restores; the swelling and pain of muscle and soft tissue disappear significantly; the small superficial wounds basically heal and the wounds can directly touch with water after a few hours.

Several cases of using the anti-inflammatory, analgesic and fast-healing external traditional Chinese medicine liniment according to the present invention are specifically provided in the following, and the following patients use the product obtained in embodiment 1.

Typical Case 1

Mr. Wang, aged 65, had a history of lumbar disc herniation for eleven years and could not straighten his back to walk year in year out due to the pain. When the pain is severe, it was often required to use the traction, frequency spectrum therapy, acupuncture, massage, drug smearing and applying plaster ways to relieve the pain and numbness, but the effect is not ideal. The lumbar pain relieved significantly in the next day after the trial of the product. He applied 10-12 drops of the product once respectively each morning and evening. When a bottle of the product (25 ml) is used up after half a month, the pain basically disappeared. Since then, he applied the product once a day and insisted on using 6 bottles until any pain of lumbar disc herniation disappeared completely. There is no recurrence of lumbar disc herniation more than five years since then.

Typical Case 2

Ms. Kuang, aged 53, suffered from cervical bone hyperplasia for seven years. The affected part was stiff and had a sharp pain. She felt dizzy and disgusted and had numbness of arm in severe case. She was troubled by the disease for many years and used many ways such as applying plasters, cupping therapy, traction treatment and surgical treatment, but these ways can only temporarily relieve the pain and the oppression symptom appeared again soon. She applied 10-12 drops of the product according to the present invention once respectively each morning and evening, and applied it on the back neck and rubbed it until it was absorbed completely. Two days later, the stiffness of neck and shoulder relieved. The neck pain disappeared and the dizziness also significantly relieved after continuous use for half a month. After using 3 bottles (25 ml per bottle), the cervical spine pain disappeared completely. So far, four years have passed and there is no any recurrence and the effect is very ideal.

Typical Case 3

Mr. Deng, aged 77, suffered from gout for many years and his right foot thumb was red and swollen year in year out. When the disease recurs, it was required to receive the infusion anti-inflammation treatment in hospital; generally, the symptom can be relieved after treatment for about 14 days and the process is very painful. A few years ago, the gout recurred again and Mr. Deng started trying to use the product according to the present invention in the case of oral medication without relief. He applied 15 drops of the product directly on the affected right foot thumb and rubbed it, then the pain significantly relieved. Since then, when the affected part is painful every day, the product would be used. Three days later, the swelling and pain of right foot thumb disappeared and he could wear shoes for a normal walk on the fourth day. The product according to the present invention is used externally in the treatment and the infusion treatment is not conducted, which eliminates the fear of side effects of oral medication on the liver and kidney, and the perennial redness and swelling of right foot thumb also disappear.

Typical Case 4

Mr. Zhao, aged 45, suffered from left knee meniscus injury due to improper exercise and there was the effusion of knee joint found through the magnetic resonance imaging. The pain was obvious when walking up and down stairs. The pain relieved on the day of using the product according to the present invention. He applied 10-12 drops of the product on the affected part once a day and rubbed it for two consecutive months, then the symptom disappeared completely. The magnetic resonance imaging results showed that the effusion of knee joint has completely disappeared and the meniscus injury also healed. So far, three years have passed and the symptom never recurs.

Typical Case 5

Ms. Li, aged 43, missed two steps of stairs when walking and her right foot instep hit the ground, and she was taken to a hospital emergency room. The filming inspection results showed that there was bone fracture, severe soft tissue contusion and severe ankle bruise. The attending doctor suggested wearing cast but Ms. Li refused to do so due to attending the provincial people's congress. She went home directly and applied the product according to the present invention every half an hour; the bruise has basically disappeared before going to bed at that night, and the swelling significantly relieved and the pain also disappeared completely. She applied the product four times in the next day and 10-12 drops each time, then the bruise significantly relieved and there was no any discomfort. On the third day (Monday), she wore high heels and took a train to attend the meeting. She has fully returned to normal through the filming review after two months.

Typical Case 6

Mrs. Fan, aged 52, has poor healing of wounds. She is extremely vulnerable to infection when there is a wound on her hands. Once, she rinsed the wound directly with tap water when the fruit knife cuts her finger, and then she dropped the product according to the present invention on the wound; the blood was stopped immediately and the wound basically healed after two hours. On the same day, she could wash the dishes directly with the injured hand again.

Typical Case 7

Ms. Qi, aged 51, suffered from left arm swelling, ulceration and infection over the years due to mosquito bite ten years ago. She used the external traditional Chinese medicine liniment according to the present invention by chance and her several wounds were festered and suppurated at that time. After the product according to the present invention was dropped on the affected part for ten hours, all the ulcerated surfaces basically scabbed and the affected part basically returned to normal after continuous use of the product for seven days.

Typical Case 8

Ms. Yang, aged 22, a ballet dancer studying in Russia, had a serious sprain on her feet. After three days of applying the product, her swelling and pain completely disappeared. On the fifth day, she could participate in the ballet performance.

Embodiment 4

The embodiment provides an anti-inflammatory, analgesic and fast-healing external traditional Chinese medicine spray, wherein the traditional Chinese medicine spray is prepared from the following raw materials in parts by weight:

| | |
|---|---|
| corydalis tuber | 40; |
| maifanitum | 90; |
| radix aconiti kusnezoffii praeparata | 35; |
| common clubmoss herb | 30; |
| clematis root | 28; |
| safflower | 25; |
| bryozoatum | 20; and |
| oyster shell | 10. |

A method for preparing the above anti-inflammatory, analgesic and fast-healing external traditional Chinese medicine spray comprises steps of: (step 1) weighing the corydalis tuber, radix aconiti kusnezoffii praeparata, common clubmoss herb, *clematis* root and safflower based on a raw material ratio, breaking cell wall and smashing the corydalis tuber, radix aconiti kusnezoffii praeparata, common clubmoss herb, *clematis* root and safflower, mixing the smashed raw materials, extracting active ingredients thereof in a closed temperature controlled extraction tank at 60° C. by taking ethanol with a mass fraction of 50% as a solvent, obtaining an extracting solution, concentrating the extracting solution under reduced pressure, and obtaining an alcohol-free concentrate; (step 2) mixing after smashing the maifanitum, bryozoatum and oyster shell, extracting active ingredients thereof in the closed temperature controlled extraction tank at 60° C. by taking sulfuric acid with a mass fraction of 2% as the solvent, and obtaining an extracting solution; and (step 3) mixing the alcohol-free concentrate obtained in the (step 1) with the extracting solution obtained in the (step 2), obtaining a mixed solution, shearing the mixed solution with an ultra-high shear homogenizer at a high speed for 20 minutes, and obtaining the anti-inflammatory, analgesic and fast-healing external traditional Chinese medicine spray.

Embodiment 5

The embodiment provides an anti-inflammatory, analgesic and fast-healing external traditional Chinese medicine ointment, wherein the traditional Chinese medicine ointment is prepared from the following raw materials in parts by weight:

| | |
|---|---|
| corydalis tuber | 40; |
| maifanitum | 90; |
| radix aconiti kusnezoffii praeparata | 35; |
| common clubmoss herb | 30; |
| clematis root | 28; |
| safflower | 25; |
| bryozoatum | 20; and |
| oyster shell | 10. |

A method for preparing the above anti-inflammatory, analgesic and fast-healing external traditional Chinese medicine ointment comprises steps of: (step 1) weighing the corydalis tuber, radix aconiti kusnezoffii praeparata, common clubmoss herb, *clematis* root and safflower based on a raw material ratio, breaking cell wall and smashing the corydalis tuber, radix aconiti kusnezoffii praeparata, common clubmoss herb, *clematis* root and safflower, mixing the smashed raw materials and extracting active ingredients thereof in a closed temperature controlled extraction tank at 50° C. by taking water as a solvent, obtaining an extracting solution, concentrating the extracting solution under reduced pressure, and obtaining an alcohol-free concentrate; (step 2) mixing after smashing the maifanitum, bryozoatum and oyster shell, extracting active ingredients thereof in the closed temperature controlled extraction tank at 60° C. by taking acetic acid with a mass fraction of 20% as the solvent and obtaining an extracting solution; and (step 3) mixing the alcohol-free concentrate obtained in the (step 1) with the extracting solution obtained in the (step 2), obtaining a mixed solution, shearing the mixed solution with an ultra-high shear homogenizer at a high speed for 20 minutes, concentrating the sheared solution, and obtaining the anti-inflammatory, analgesic and fast-healing external traditional Chinese medicine ointment.

Through the observation and analysis of trial of patients, the anti-inflammatory, analgesic and fast-healing external traditional Chinese medicine spray and ointment prepared in the above embodiment 4 and embodiment 5 are very effective in treating the pain of bone and joint, muscle and soft tissue, and the affected part can basically achieve a satisfactory degree of recovery after continuous use for a period of time. For the crowd of small superficial wounds, the traditional Chinese medicine preparation according to the present invention has a prominent effect in anti-inflammation, relieving pain and healing wounds.

The present invention has many specific applications and the above description is only the preferred embodiments of the present invention. It should be noted that the above embodiments are only for illustrating the present invention and are not intended to limit the protection scope of the present invention. Several improvements can be made without departing from the principle of the present invention for ordinary persons skilled in the art and such improvements shall also be considered as having been covered by the protection scope of the present invention.

What is claimed is:

1. An anti-inflammatory, analgesic and fast-healing external traditional Chinese medicine preparation, which comprises following components in parts by weight:

| | |
|---|---|
| corydalis tuber | 30-80; |
| maifanitum | 20-90; |
| radix aconiti kusnezoffii praeparata | 20-50; |
| common clubmoss herb | 10-45; |
| clematis root | 10-40; |
| safflower | 10-40; |
| bryozoatum | 5-40; and |
| oyster shell | 5-35. | wherein the corydalis tuber, radix aconiti kusnezoffii praeparata, common clubmoss herb, clematis root and safflower are prepared by steps of:

(A1) mixing after breaking cell wall and smashing corydalis tuber raw material, radix aconiti kusnezoffii praeparata raw material, common clubmoss herb raw material, clematis root raw material and safflower raw material according to the parts, extracting active ingredients of the mixed corydalis tuber raw material, radix aconiti kusnezoffii praeparata raw material, common clubmoss herb raw material, clematis root raw material and safflower raw material in a closed temperature controlled extraction tank at 40-60° C. by taking ethanol with a mass fraction in a range of 50-70% or water as a solvent, obtaining a first extracting solution, distilling the first extracting solution under reduced pressure, and obtaining an alcohol-free concentrate;

(A2) mixing after smashing maifanitum raw material, bryozoatum raw material and oyster shell raw material according to the parts, extracting active ingredients of the mixed maifanitum raw material, bryozoatum raw material and oyster shell raw material in the closed temperature controlled extraction tank at 40-60° C. by taking sulfuric acid with a mass fraction in a range of 2-10% or acetic acid with a mass fraction in a range of 2-20% as a solvent, and obtaining a second extracting solution; and (A3) mixing the alcohol-free concentrate obtained in the step (A1) with the second extracting solution obtained in the step (A2), obtaining a mixed solution, and shearing the mixed solution with an ultra-high shear homogenizer for 20 minutes, thereby obtaining the anti-inflammatory, analgesic and fast-healing external traditional Chinese medicine preparation.

2. The anti-inflammatory, analgesic and fast-healing external traditional Chinese medicine preparation according to claim 1, wherein in the step (A1), the active ingredients of the mixed corydalis tuber raw material, radix aconiti kusnezoffii praeparata raw material, common clubmoss herb raw material, clematis root raw material and safflower raw material are extracted in the closed temperature controlled extraction tank at 60° C. by taking ethanol with the mass fraction of 60% as the solvent; in the step (A2), the active ingredients of the mixed maifanitum raw material, bryozoatum raw material and oyster shell raw material are extracted in the closed temperature controlled extraction tank at 40-60° C. by taking sulfuric acid with the mass fraction of 10% as the solvent.

3. The anti-inflammatory, analgesic and fast-healing external traditional Chinese medicine preparation according to claim 1 in a dosage form selected from the group consisting of a liniment, spray and ointment.

4. The anti-inflammatory, analgesic and fast-healing external traditional Chinese medicine preparation according to claim 2 in a dosage form selected from the group consisting of a liniment, spray and ointment.

* * * * *